(12) United States Patent
Mogg (10) Patent No.: US 7,749,199 B2
(45) Date of Patent: Jul. 6, 2010

(54) CATHETER CLAMP

(75) Inventor: Alan David Mogg, Dorset (GB)

(73) Assignee: Goma Medical Limited, Wimborne, Dorset (GB)

( * ) Notice: Subject to any disclaimer, the term of this patent is extended or adjusted under 35 U.S.C. 154(b) by 0 days.

(21) Appl. No.: 10/915,322

(22) Filed: Aug. 11, 2004

(65) Prior Publication Data

US 2005/0054985 A1 Mar. 10, 2005

Related U.S. Application Data

(63) Continuation-in-part of application No. PCT/GB03/00539, filed on Feb. 12, 2003.

(30) Foreign Application Priority Data

Feb. 16, 2002 (GB) ................................ 0203713.3

(51) Int. Cl.
*A61M 5/32* (2006.01)
(52) U.S. Cl. ...................................... 604/174; 604/178
(58) Field of Classification Search ................ 604/174, 604/171, 177, 178–180, 264, 523; 128/DIG. 6, 128/DIG. 26
See application file for complete search history.

(56) References Cited

U.S. PATENT DOCUMENTS

| | | | |
|---|---|---|---|
| 4,533,349 A | 8/1985 | Bark | |
| 4,659,329 A | 4/1987 | Annis | |
| 5,372,589 A * | 12/1994 | Davis | .......................... 604/180 |
| 5,690,616 A | 11/1997 | Mogg | |
| 6,387,076 B1 * | 5/2002 | Landuyt | ....................... 604/174 |
| 6,482,183 B1 * | 11/2002 | Pausch et al. | ................ 604/174 |

FOREIGN PATENT DOCUMENTS

| | | |
|---|---|---|
| DE | 19749741 | 11/1998 |
| DE | 19749741 C1 * | 11/1998 |
| EP | 0327299 | 8/1989 |
| GB | 2147811 | 5/1985 |
| GB | 2288538 | 10/1995 |
| WO | WO 99/24103 | 5/1999 |

* cited by examiner

*Primary Examiner*—Nicholas D Lucchesi
*Assistant Examiner*—Laura A Bouchelle
(74) *Attorney, Agent, or Firm*—Baker Botts LLP (57) ABSTRACT

A catheter clamp includes a body portion and clamp, the body portion comprising a first location portion which receives a catheter which issues from a patient's skin, a second location portion which causes the catheter to be bent through an arc and a third location portion which guides the catheter to an exit of the clamp, the third location portion comprising side walls which flank the catheter so as to form a close-fitting pathway, the arrangement of the clamp being such that in use the clamp is manually operable and can be caused to adopt a clamping condition in which the clamping portion clamps at least one of that portion of the catheter which is located by the third location portion and that portion of the catheter which is located by the second location portion. The inventive catheter clamp is advantageously of a lower profile than known catheter clamps.

14 Claims, 8 Drawing Sheets

CATHETER CLAMP

CROSS-REFERENCE TO RELATED APPLICATIONS

The present application is a continuation-in-part of PCT/GB03/00539, which was filed on Feb. 12, 2003, and which claims the priority of GB 0203713.3, which was filed on Feb. 16, 2002. The entire contents of PCT/GB03/00539 and GB 0203713.3 are incorporated herein by reference.

The present invention relates to catheter clamps for attaching catheters to patients' skin at an insertion site.

Catheters can be inserted into patients where there is a requirement, for example, to administer continuous or repeated does of analgesia, such as epidurals, spinals or nerve blocks, or to provide intravenous feed lines, chest drains etc.

Catheters are typically flexible tubes of small diameter which are difficult to hold and consequently easily pulled from the patient or the end displaced, thereby causing ineffective pain control when used to administer analgesia. Also flexure of the catheter can cause analgesia to leak back along the outside of the catheter.

Catheter clamps are known which seek to overcome those disadvantages. Some known clamps, despite their ability to provide good clamping nevertheless have, over time, shown that there is scope for further development of catheter clamps.

U.S. Pat. No. 5,690,616 discloses a catheter clamp in which on exiting an arcuate location portion the catheter enters into a region of open space and not into a location portion which comprises side-walls that flank the catheter so as to form a close-fitting pathway.

DE 19749741C1 discloses a catheter clamp in which the body portion alone does not form a third location portion that comprises walls that flank the catheter so as to form a close-fitting pathway. Rather the clamp cover and the body together purportedly form a close-fitting pathway.

The present invention seeks to provide an improved catheter clamp.

According to a first aspect of the invention there is provided a catheter clamp comprising a body portion and a clamping means, the body portion comprising catheter location means which defines a passageway, the catheter location means comprising a first location portion which receives a catheter which issues from a patient's skin, a second location portion which causes the catheter to be bent through an arc and a third location portion which guides the catheter to an exit of the clamp, the first, second and third location portions each being provided at a different longitudinal position along the passageway, the arrangement of the clamp being such that in use the clamping means is manually pivotable to adopt a clamping condition in which the clamping portion clamps at least one of that portion of the catheter which is located by the third location portion and that portion of the catheter which is located by the second location portion, characterised in that the third location portion comprises a base that supports the catheter, and further comprises side walls which flank the catheter so as to form a close-fitting pathway.

In a preferred embodiment of the invention the fact that the clamping means is arranged to engage with that portion of the catheter which is located by a channel which guides the catheter to the exit of the device advantageously allows the device to be of a lower profile on a patient's skin. Such a lower profile alleviates a clinician's perception of discomfort of the clamp when in situ.

Preferably the clamping means comprises a hinge and an arm, the hinge pivotally mounting the arm to the body portion.

Preferably the arm comprises arm retention means adapted to hold the arm in a clamping condition, said arm retention means comprising co-operating formations provided on said arm and on the body portion.

Most preferably the hinge and the arm are provided substantially diametrically of the clamping portion.

The clamping means preferably comprises a clamping surface which has a longitudinal cross-sectional profile which is substantially the same as that of the third location portion.

In the clamping condition the clamping means desirably at least partially encloses a region in which the insertion site is located.

Preferably, in the clamping condition respective complementary interface surfaces of the clamping means and the body bear against each other to form a barrier to the insertion site which substantially prevents an ingress of bacteria.

Advantageously since the clamping means provides such a barrier the need, with its attendant cost, for applying a dressing is obviated.

In a preferred embodiment the clamping means comprises a cap which is provided with a substantially transparent portion through which the insertion site may be viewed, whereas applying a dressing to a known clamp can inhibit a clear view of the site. A further disadvantage of the application of a dressing is that such makes release of the clamp for access to the insertion site potentially problematic and cumbersome.

The clamping means preferably comprises a formation in the respective bearing surface which in part allows the catheter to exit the device. In a preferred embodiment the formation results in a close-fitting arrangement.

The third location portion preferably comprises catheter gripping means which at least substantially restricts movement of the catheter in a direction which is substantially parallel to a longitudinal axis of the third location portion.

The gripping means preferably comprises a rib which extends substantially perpendicular to the longitudinal axis of the third location portion. Most preferably a plurality of such ribs is provided.

The body portion preferably comprises viewing means which allows a region proximal to the insertion site to be viewed. The viewing means is preferably provided by at least one aperture.

One embodiment of the invention will now be described, by way of example only, with reference to the accompanying drawings in which.

Figure 1:
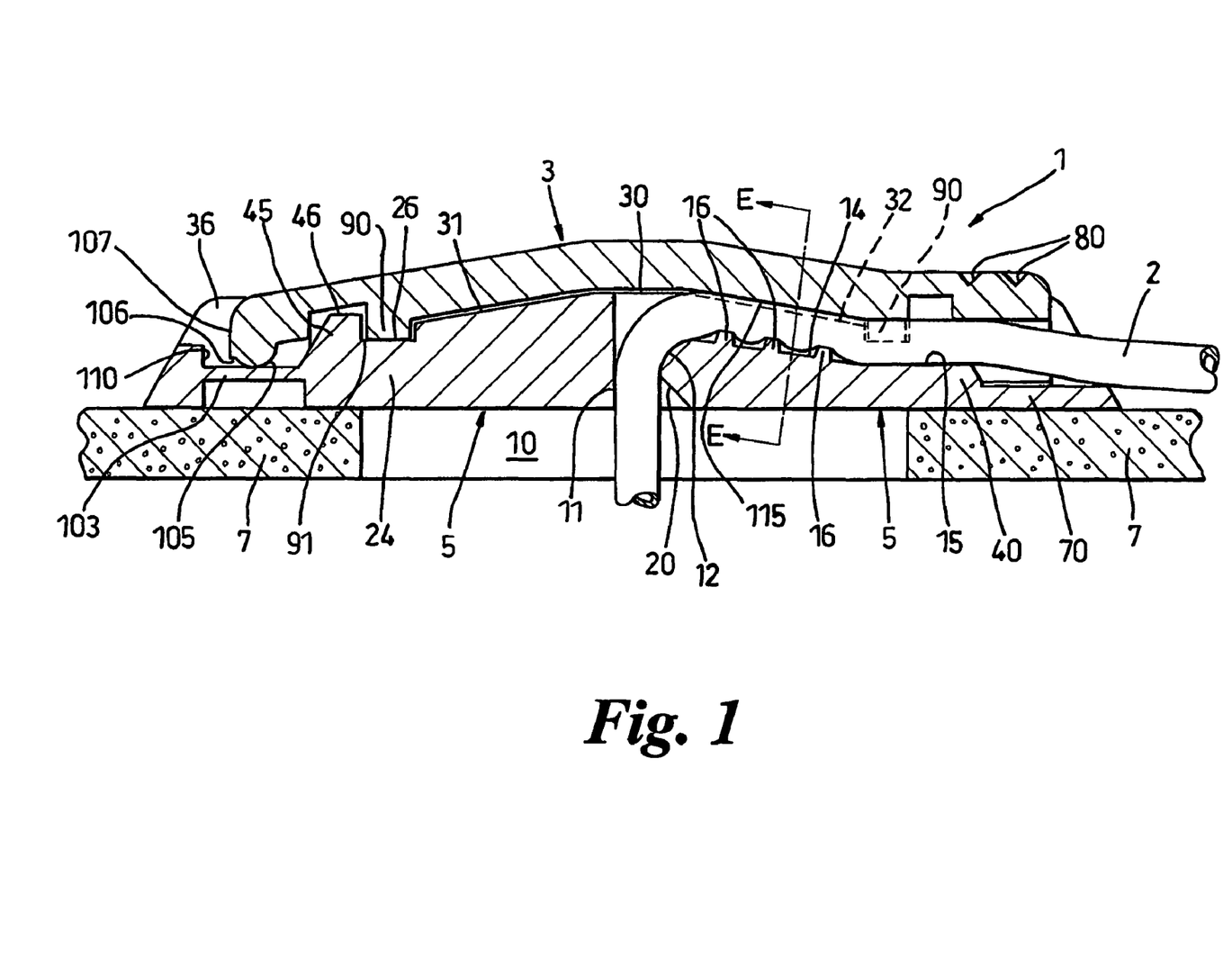
FIG. 1 is a cross-sectional view of a catheter clamp in a clamping condition and a catheter on A-A.

With reference initially to FIG. 1 there is shown a catheter clamp 1 comprising a body 5 and a cap 3 of arm-like form, the cap 3 being pivotally mounted with respect to the body. The arrangement of the clamp 1 being such that in the clamping condition shown in FIG. 1 the cap 3 acts upon a catheter 2 so as to clamp the catheter between the cap and the base.

The body 5 is adhered to a mounting pad 7 which is made of a closed-cell resilient foam material. The mounting pad 7 is provided with an aperture 10 which is substantially central of the body 5.

The body 5 comprises location means in the form of a passageway which comprises a first location portion 11, a second location portion 12 and a third location portion 13. A semi-circular vertical wall 11 defines the first location portion.

The second location portion is defined by a curved edge portion 12 whose surface extends from a substantially vertically orientation to a substantially horizontal orientation.

The third location portion 13 comprises an inclined channel 14 and a substantially horizontal channel portion 15.

The inclined channel 14 comprises three equi-spaced ribs 16 which extend substantially perpendicular to the longitudinal axis of said inclined channel.

Figure 2:
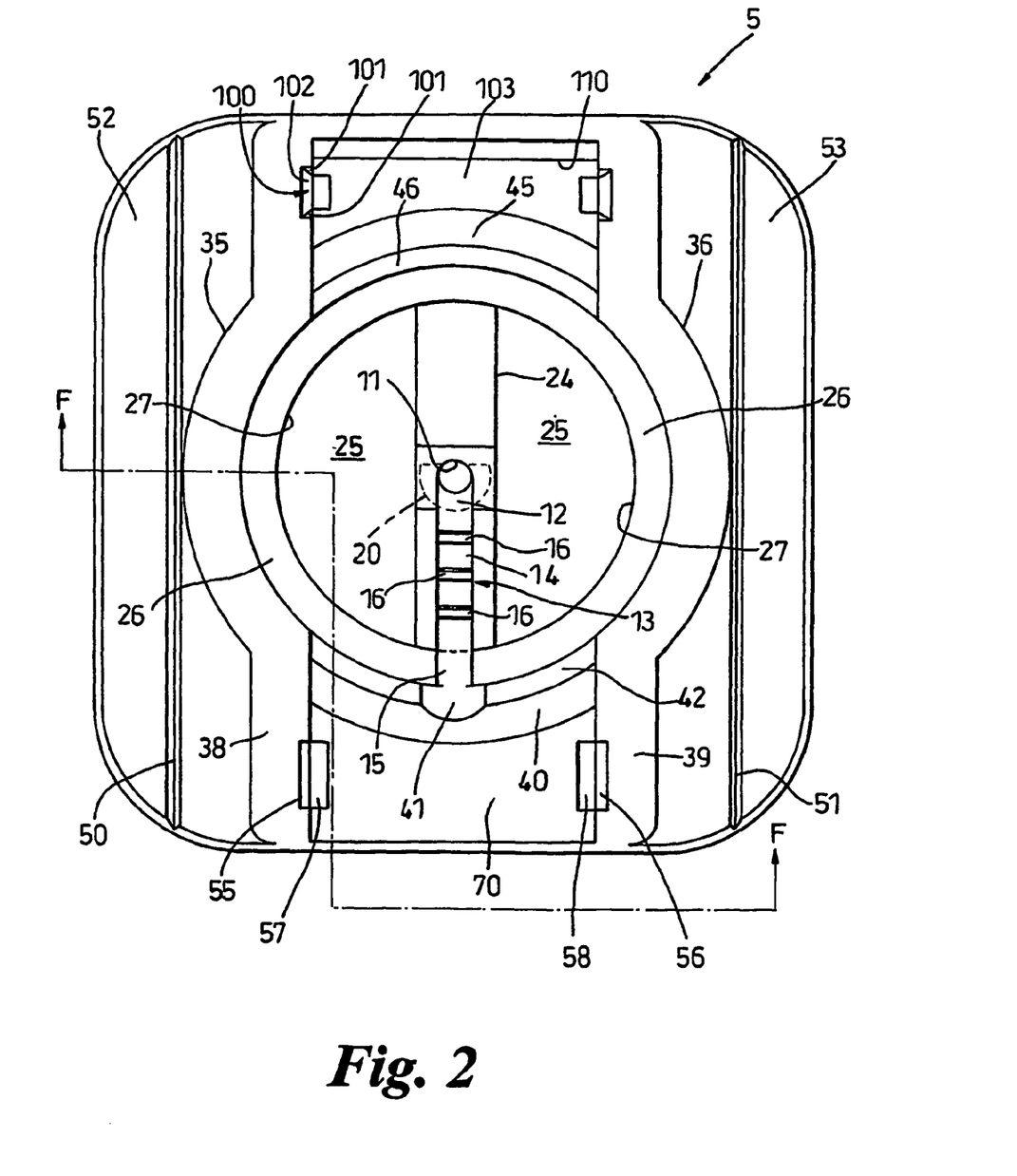
FIG. 2 is a plan view of the body of the catheter clamp shown in FIG. 1 in which the cap of the clamp, the catheter and the mounting pad have been omitted for clarity.

The first location portion 11, the second location portion 12 and the inclined channel portion of the third location portion are formed in a bridge portion 24, the bridge portion 24 extending diametrically across a circular space which is defined by the radially inwardly directed surfaces 27 (as best seen in FIG. 2).

As viewed in FIG. 1 the bridge portion 24 comprises two flat uppermost surfaces 30, an inclined surface 31 and two inclined surfaces 32 which flank the inclined channel 15. The surfaces 27 and the bridge section 24 define two substantially D-shaped apertures which are located on each side of the bridge portion.

Adjacent and perpendicular to the radially inwardly directed surfaces 27 there is provided an upwardly facing part-annular interface surface 26, as best seen in FIG. 2.

Standing proud of the interface surface 26 there are provided two tapered side walls 35 and 36 which are situated at each side of the interface surface 26 and extend along the length of the body. Each side wall each comprises two substantially straight portions interposed by a central arcuate portion.

The horizontal channel portion 15 is provided by a recess in a tapered front wall 40 which is of arcuate outline, the recess being aligned with the inclined channel 14.

The horizontal channel portion 15 is provided by a recess formed in the interface surface 26 and is aligned with the inclined channel 14. An inclined front wall 40 is formed with a recess 41 which is aligned with the channel portion 15.

The front wall 40 comprises an upper surface 42 which is at a level which is above the vertical level of the interface surface 26, but below the vertical level of the side walls 35 and 36.

The body 5 further comprises a tapered rear wall 45 of arcuate outline which is located adjacent to the interface surface 26. The rear wall 45 comprises an upper surface 46 which is of substantially part-annular shape and is concentric with the interface surface 26.

Hinge grooves 50 and 51 are provided to each side of side walls 35 and 36 respectively. The hinge grooves 50 and 51 being attached to hinged portions 52 and 53 respectively.

Those portions (referenced 38 and 39) of the side walls 35 and 36 which are located towards the front end of the body 5 are provided on their respective inwardly facing surfaces with recesses 55 and 56 which taper downwardly. Downwardly facing flange portions 61 and 62 are provided on an underside of the portions 38 and 39. Two moulding recesses 57 and 58 are located proximal to the side wall portions 38 and 39 which extend through a base portion 70 of the body and into said wall portions.

Figure 3:
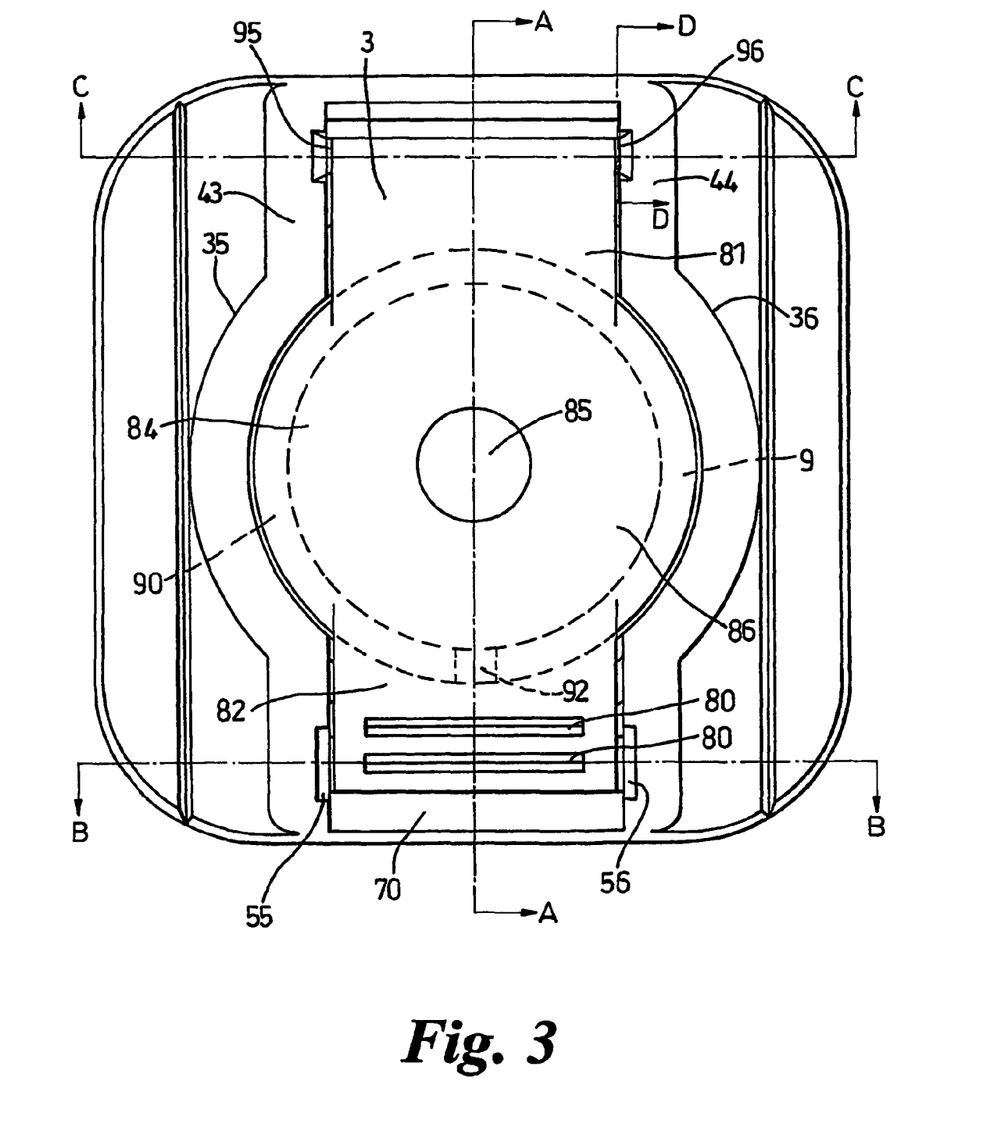
FIG. 3 is a plan view of the clamp shown in FIGS. 1 and 2 in a closed condition in which the catheter and the mounting pad have been omitted for clarity.
Figure 4:
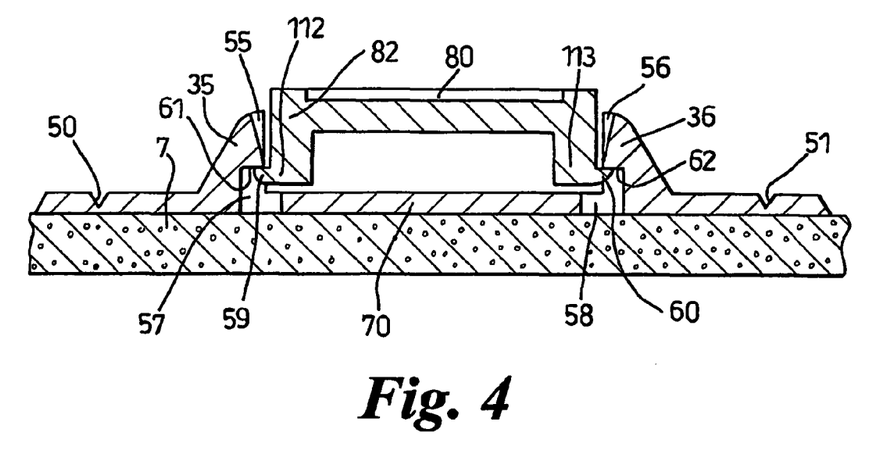
FIG. 4 is a cross-sectional view of the clamp in the clamping condition as shown in FIG. 3 on B-B.
Figure 5:
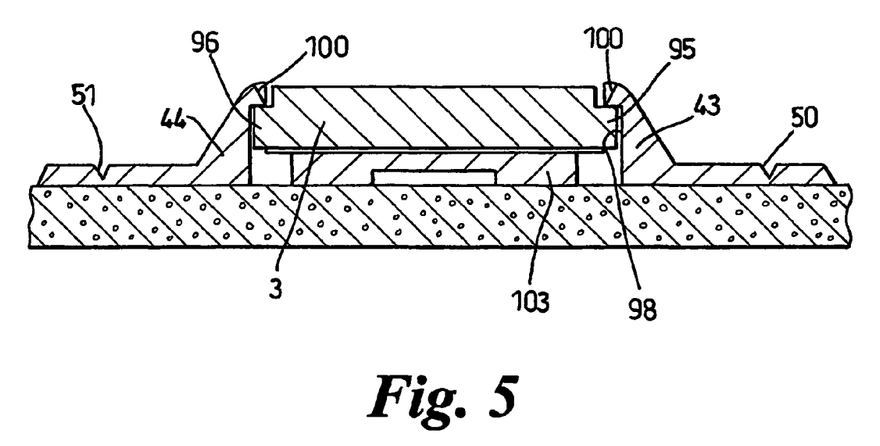
FIG. 5 is a cross-sectional view of the clamp in the clamping condition as shown in FIG. 3 on C-C.
Figure 6:
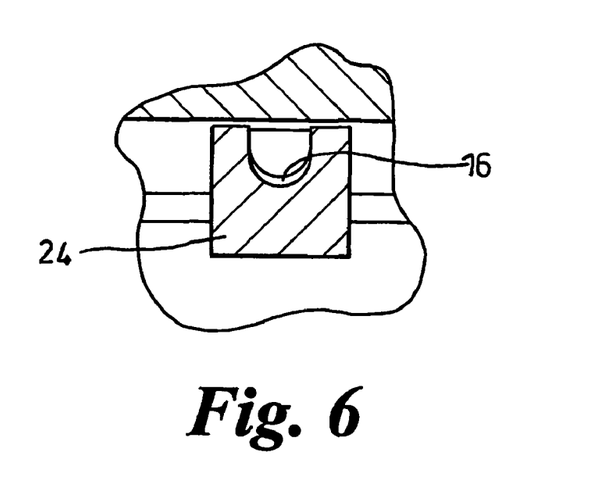
FIG. 6 is a partial cross-sectional view of the location channel on E-E.
Figure 7:
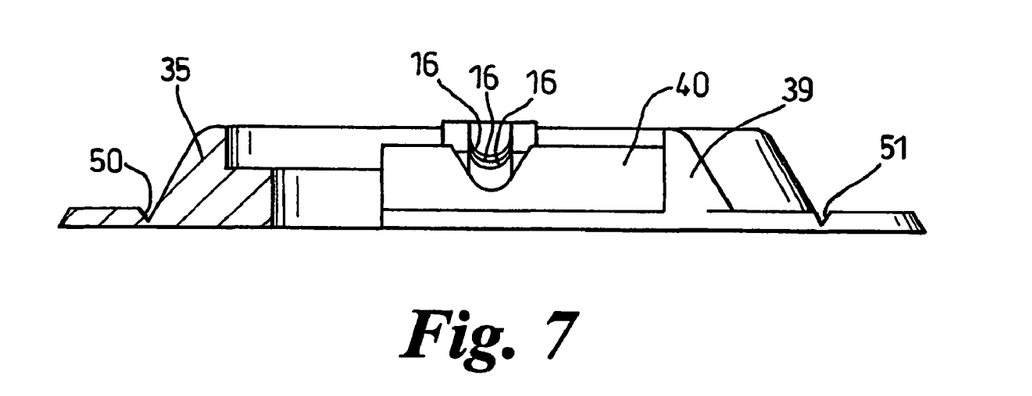
FIG. 7 is a cross-sectional view of the body of the clamp on F-F in which the mounting has been omitted for clarity.

With reference in particular to FIGS. 1, 3 and 4 the cap 3 comprises a central portion 84 of generally circular outline which is interposed between two limbs 81 and 82, said limbs being substantially diametrical to the central portion 84.

The central portion 84 is essentially of frusto-conical shape with an uppermost surface 85 and a part-conical wall 86 around said uppermost surface.

The underside of the cap 3 is provided with a downwardly extending (when viewed in the condition shown in FIG. 1) abutment 90 of part annular shape.

The abutment 90 comprises a lowermost interface surface 91 and has formed therein a substantially semi-circular shaped recess 92.

The front limb 82 comprises two spaced depending portions 112 and 113 each of which is provided with clips 59 and 60 respectively. The upper surface of the limb 82 comprises two substantially V-shaped grooves 80.

Figure 8:
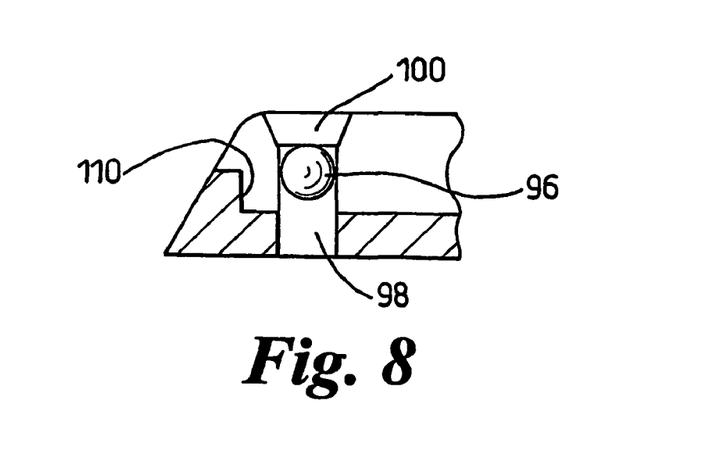
FIG. 8 is a cross-sectional view of part of the body of the clamp on D-D in which the mounting pad is omitted for clarity.

The limb 81 which is situated towards the rear of the clamp is hinged to the body by way of a pivot having rounded distal ends 95 and 96 which is integral with the cap 3. Each pivot end is located in a respective slot which is formed in the respective side wall, of which slot 98 which receives pivot end 96 is shown in FIG. 8. Vertically above each slot there is provided a tapered recess 100 which is defined by three inclined surfaces 101, 102 and 103.

Situated between the rearmost portions 43 and 44 of the side walls 35 and 36 the body 5 comprises a base portion 103. Perpendicular to the base portion 103 there is provided a wall 110.

As seen best in FIG. 1, that section of the pivot end which lies between the pivot ends 95 and 96 comprises a rounded outer surface portion 105. The rounded surface portion 105 leads to an edge protrusion 106 which is contiguous with a substantially flat surface portion 107.

The operation of the catheter clamp 1 will now be described. The clamp is assembled by initially aligning the pivot ends 95 and 96 over the respective recesses 100. The pivot ends are then urged into the recesses so as to slightly compress the pivot ends and so momentarily deflecting the wall portions 43 and 44 and guide the same into their respective slots.

The cap 3 is then caused to adopt an open condition in which said cap is substantially perpendicular to the body 5. In such a condition the flat surface portion 107 rests on the base portion 103. The wall 110 acts as a stop means to prevent the cap from being pivoted back any further than the perpendicular position.

The catheter is fed through the underside of the body 5 via the part-circular wall 11 and the part conical surface 20 until the catheter clamp can be positioned above the insertion site of the catheter (not shown). The part conical surface 20 facilitates the initial clamp positioning step.

An adhesive on the underside of the foam pad 7 is exposed by peeling away a release paper, and the adhesive contacting the patient's skin to hold the clamp in position.

The appropriate portion of the catheter is then urged into the channel portions 14 and 15 which are dimensioned so as to provide a close fitting pathway for the catheter. The catheter is thus located as shown in FIG. 1.

The apertures 25 allow the position of the insertion site to be viewed and so ensure correct location of the clamp relative to the insertion site.

The cap 3 is then pivoted generally downwardly so that the clips 59 and 60 initially engage with the tapered recesses 55 and 56 respectively. In order to pivot the cap 3 from the open condition to the closed condition, the edge protrusion 106 engages with the base portion 103 so as to deflect said base portion and thus a force needs to be overcome in order for the cap to adopt the closed condition. Further depression of the cap 3 causes the depending portions 112 and 113 to be compressed and subsequently snap into position against the flanged portions 61 and 62 of the side wall portions 38 and 39. The cap 3 is now in the clamping condition shown in FIG. 1.

In the clamping condition a portion 115 of the underside of the cap 3 engages with that portion of the catheter 2 which is located by the channel portions 14 and 15 so as to urge the catheter into said channel portions. As is evident from FIG. 1 the longitudinal cross-sectional profile of surface 115 is substantially the same as that of the channel portions 14 and 15. The ribs 16 act so as to substantially restrict movement of the catheter in a direction which is substantially parallel to the longitudinal axis of the channel portions.

In the clamping condition the interface surface 91 of the cap 3 bears against the interface surface 26 of the body 5 so as to form a barrier which substantially prevents an ingress of bacteria.

Such a barrier is achieved by forcing the surfaces 26 and 91 together sufficiently by the action of strain energy in the limbs 81 and 82. This strain energy is brought about on one hand by the co-operation between pivot ends 95 and 96 bearing against the rear side walls 44 and 45 and on the other hand by the co-operation between clips 59 and 60 bearing against the surfaces 61 and 62.

The recess 92 of the abutment 90 and the channel portion 15 form a tight grip around the respective part of the catheter by way of a tight-fitting hole and similarly prevent an ingress of bacteria.

The hinged portions 52 and 53 allow for the clamp 1 to be sited on an irregular surface so that those portions can be configured to more closely follow the contours of a patient's body.

Although in the above described and illustrated embodiment the cap 3 clamps that portion of the catheter which is located by the inclined channel 14, in a alternative embodiment of the invention the cap 3 may comprise a surface portion which in addition or alternatively that clamping action acts to clamp that portion of the catheter which is located by the curved edge 12.

Figure 9:
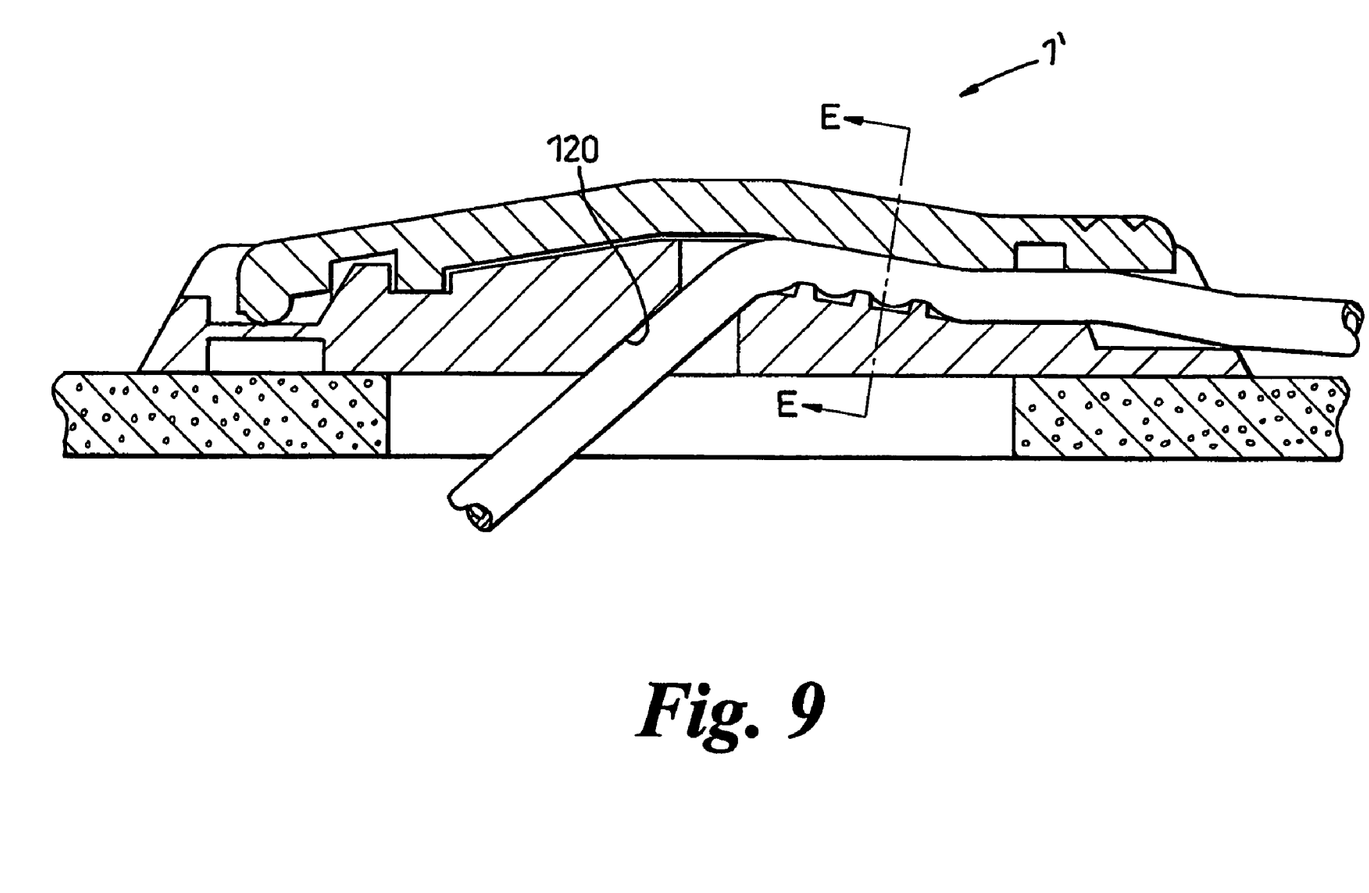
FIG. 9 is a cross-sectional view of a clamp similar to that shown in FIG. 1 in which the clamp is adapted to receive a catheter which exits the patient's skin at an angle other than 90°.
Figure 10:
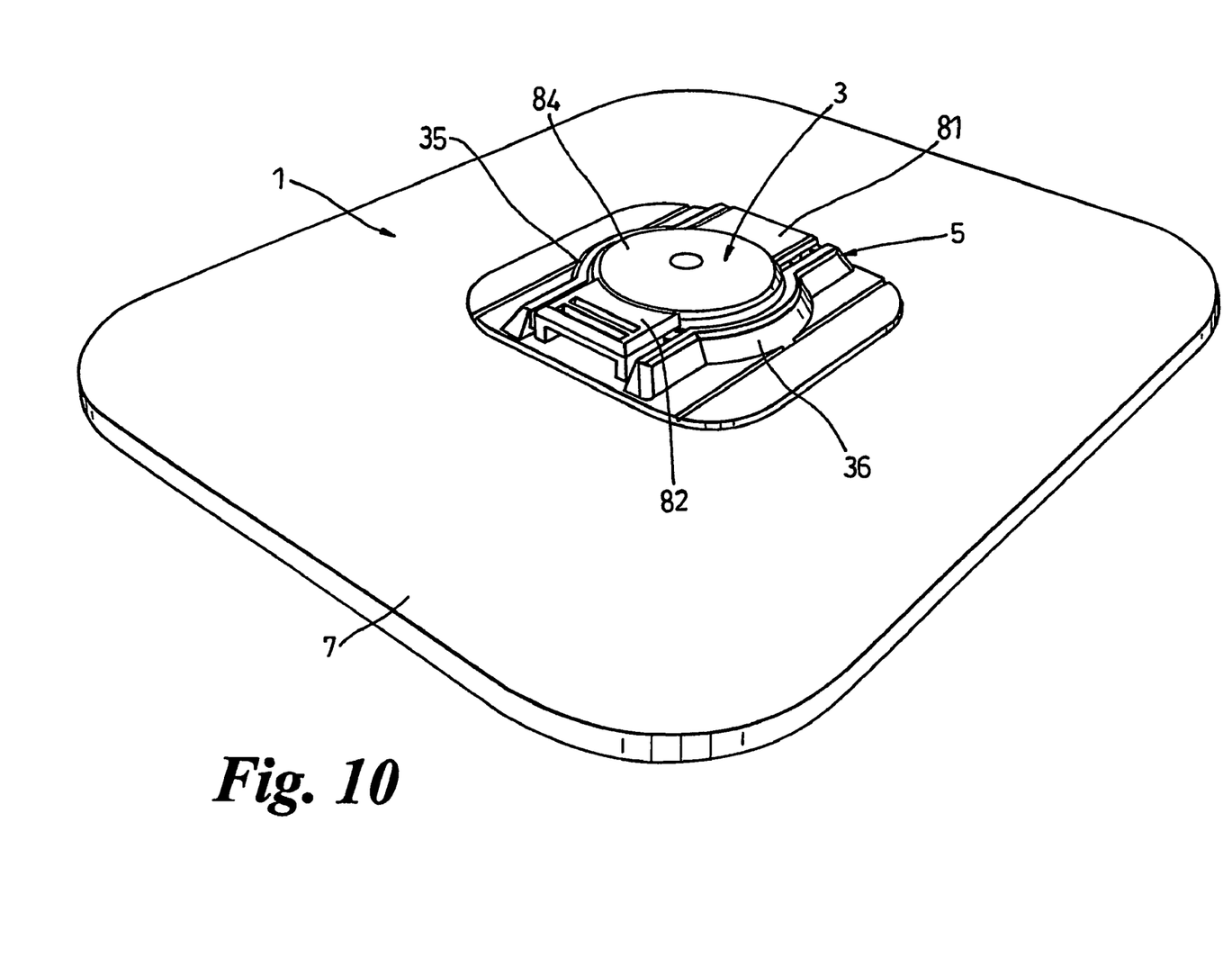
FIG. 10 shows a perspective view of the catheter clamp shown in FIG. 1 in a clamping condition in which the catheter is omitted for clarity.
Figure 11:
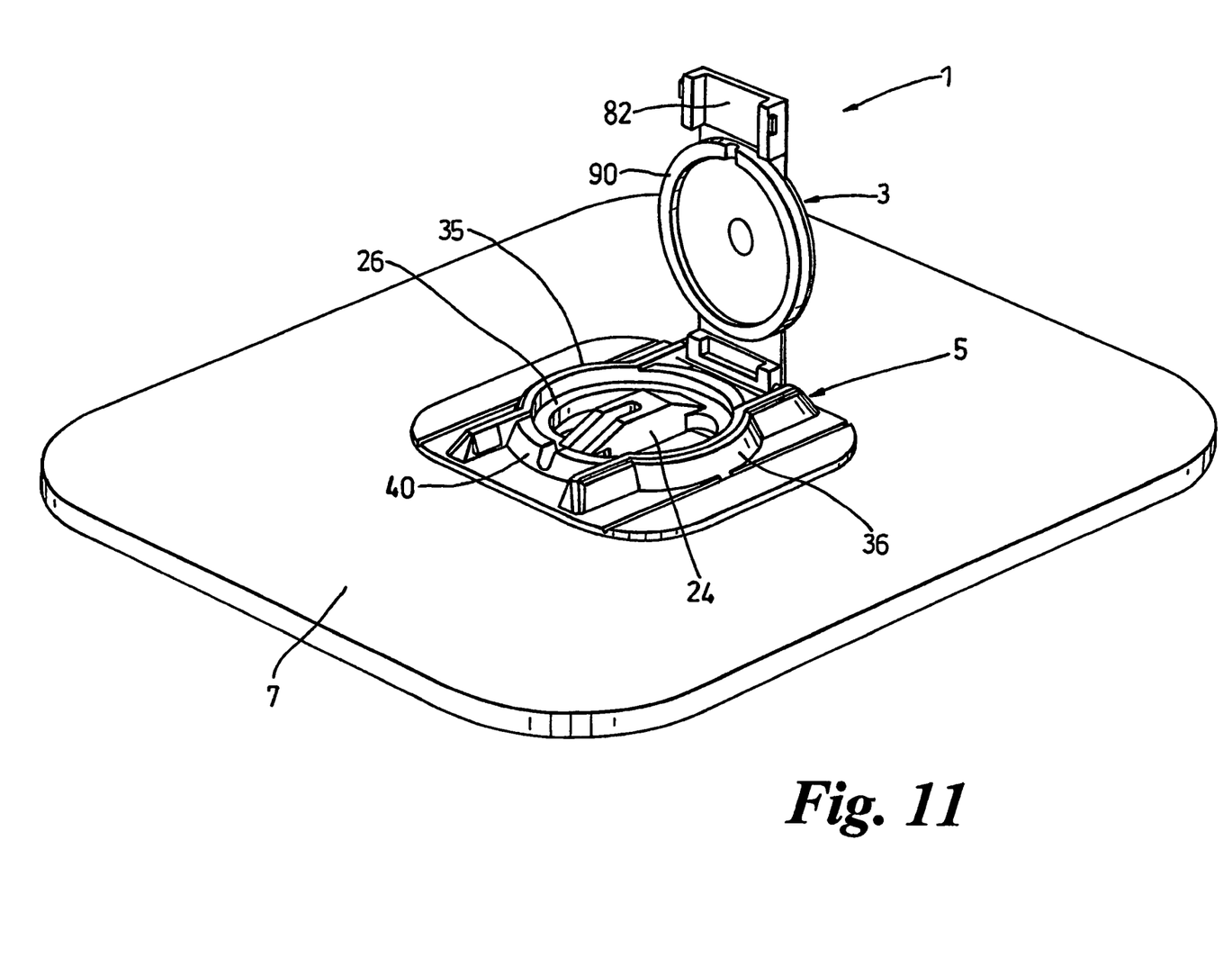
FIG. 11 shows a perspective view of the catheter clamp shown in FIG. 1 in an open condition in which the catheter is omitted for clarity.

FIG. 9 shows an alternative embodiment which is substantially identical to the clamp 1 in which a first location portion is provided by an inclined surface 120. This embodiment advantageously allows the clamp to be used with catheters which exit from the skin at an acute angle.

The invention claimed is:

1. A catheter clamp comprising a body portion and a clamping means, the body portion comprising catheter location means which defines a passageway, the catheter location means comprising a first location portion which receives a catheter which issues from a patient's skin, a second location portion which causes the catheter to be bent through an arc and a third location portion which guides the catheter to an exit of the clamp, the first, second and third location portions each being provided at a different longitudinal position along the passageway, the arrangement of the clamp being such that in use the clamping means is manually pivotable to adopt a clamping condition in which the clamping portion clamps at least one of that portion of the catheter which is located by the third location portion and that portion of the catheter which is located by the second location portion, characterised in that the third location portion comprises a base that supports the catheter, and further comprises side walls which flank the catheter, the side walls being spaced at substantially the external diameter of the catheter so as to form a close-fitting pathway, and the clamping means arranged to cause deformation of the cross-section of the catheter in the close fitting pathway when in the clamping condition.

2. A catheter clamp as claimed in claim 1, in which the second location portion comprises side walls which flank the catheter so as to form a close-fitting pathway.

3. A catheter clamp as claimed in claim 1, in which the clamping means comprises a hinge and an arm, the hinge pivotally mounting the arm to the body portion.

4. A catheter clamp as claimed in claim 3, in which the arm comprises arm retention means adapted to hold the arm in a clamping condition, said arm retention means comprising co-operating formations provided on said arm and on the body portion.

5. A catheter clamp as claimed in claim 4, in which the hinge and the arm retention means are provided substantially diametrically of the arm.

6. A catheter clamp as claimed in claim 1 in which the clamping means comprises a clamping surface which has a longitudinal cross-sectional profile which is substantially the same as that of the third location portion.

7. A catheter clamp as claimed in claim 1, in which in the clamping condition the clamping means at least partially encloses a region in which the insertion site is located.

8. A catheter clamp as claimed in claim 1, in which in the clamping condition respective complementary interface surfaces of the clamping means and the body bear against each other to form a barrier to the insertion site which substantially prevents an ingress of bacteria.

9. A catheter clamp as claimed in claim 8, in which the clamping means comprises a formation in the respective interface surface which in part allows the catheter to exit the catheter clamp.

10. A catheter clamp as claimed in claim 9, in which the third location portion comprises catheter gripping means which at least substantially restricts movement of the catheter in a direction which is substantially parallel to a longitudinal axis of the third location portion.

11. A catheter clamp as claimed in claim 10, in which the gripping means comprises a rib which extends substantially perpendicular to the longitudinal axis of the third location portion.

12. A catheter clamp as claimed in claim 11, in which a plurality of ribs is provided.

13. A catheter clamp as claimed in claim 1, in which the body portion comprises viewing means which allows a region proximal to the insertion site to be viewed.

14. A catheter clamp as claimed in claim 13, in which the viewing means is provided by at least one aperture.

* * * * *